United States Patent
Shetty et al.

(10) Patent No.: US 11,050,875 B1
(45) Date of Patent: Jun. 29, 2021

(54) CONDUCTING AUTOMATED CONTENT PROCESSING TO IDENTIFY POLICY COMPLIANCE

(71) Applicant: West Corporation, Omaha, NE (US)

(72) Inventors: Santhosh Shetty, Omaha, NE (US); Karen Sue White, Omaha, NE (US)

(73) Assignee: West Corporation, Omaha, NE (US)

( * ) Notice: Subject to any disclaimer, the term of this patent is extended or adjusted under 35 U.S.C. 154(b) by 0 days.

(21) Appl. No.: 16/421,190

(22) Filed: May 23, 2019

(51) Int. Cl.
*H04M 3/22* (2006.01)
*G16H 15/00* (2018.01)
*G16H 50/30* (2018.01)
*G10L 15/18* (2013.01)

(52) U.S. Cl.
CPC ....... *H04M 3/2218* (2013.01); *G10L 15/1815* (2013.01); *G16H 15/00* (2018.01); *G16H 50/30* (2018.01)

(58) Field of Classification Search
USPC ... 379/162, 265.09, 142.05, 85, 67.1, 202.1, 379/203.01, 265.12
See application file for complete search history.

(56) References Cited

U.S. PATENT DOCUMENTS

| | | | |
|---|---|---|---|
| 9,225,833 B1* | 12/2015 | Koster | H04M 3/42221 |
| 9,936,066 B1* | 4/2018 | Mammen | G10L 15/26 |
| 10,123,078 B1* | 11/2018 | McCarty | H04N 21/4668 |
| 10,708,425 B1* | 7/2020 | Hernandez | H04M 3/5175 |
| 2010/0241577 A1* | 9/2010 | Geppert | H04M 3/5233 705/304 |
| 2010/0332227 A1* | 12/2010 | Melamed | G06Q 10/06395 704/236 |
| 2014/0257852 A1* | 9/2014 | Walker | G16H 50/20 705/3 |
| 2017/0353605 A1* | 12/2017 | Dumaine | G06Q 10/063112 |
| 2018/0091654 A1* | 3/2018 | Miller | G06Q 50/2057 |
| 2019/0037077 A1* | 1/2019 | Konig | H04M 3/5183 |
| 2019/0108834 A1* | 4/2019 | Nelson | G06Q 10/10 |

* cited by examiner

*Primary Examiner* — Maria El-Zoobi

(57) ABSTRACT

One example method of operation may include identifying a call scheduled for a scheduled time having a calling party profile and a called party profile, identifying one or more calling party flags associated with the calling party profile and one or more called party flags associated with the called party profile, establishing a call connection between a calling party device and a called party device at the scheduled time to conduct the call, recording call content identified during the call, processing the call content of the recorded call to identify call content compliance based on the calling party flags and the called party flags, scoring the call based on the identified call content compliance, and updating one or more of the called party profile and the calling party profile to identify the scored call.

14 Claims, 5 Drawing Sheets

US 11,050,875 B1

CONDUCTING AUTOMATED CONTENT PROCESSING TO IDENTIFY POLICY COMPLIANCE

TECHNICAL FIELD OF THE APPLICATION

This application relates to automated content processing, and more specifically to conducting automated content processing to identify compliance measures.

BACKGROUND OF THE APPLICATION

Conventionally, phone calls and other types of communications between certain parties often take place without a review or feedback procedure. In general, phone calls are private matters which are not recorded and listened to by others except in rare instances. On the other hand, phone calls are important when there are liability issues at stake, such as between doctor and patient.

A patient may be readily identified as having various conditions and requiring various types of screening, bedside manner (e.g., approach by doctor), questions, and answers in order to cover a track of liability for that patient. Also, the doctor may require training and/or may need assistance improving certain behaviors towards patients to ensure compliance with hospital safety standards. The content of a call may be recorded and analyzed to identify whether the call was conducted in a manner consistent with company standards or other rules and regulations.

SUMMARY OF THE APPLICATION

Example embodiments of the present application provide at least a method that includes at least one of identifying a call scheduled for a scheduled time comprising a calling party profile and a called party profile, identifying one or more calling party flags associated with the calling party profile and one or more called party flags associated with the called party profile, establishing a call connection between a calling party device and a called party device at the scheduled time to conduct the call, recording call content identified during the call, processing the call content of the recorded call to identify call content compliance based on the calling party flags and the called party flags, scoring the call based on the identified call content compliance, and updating one or more of the called party profile and the calling party profile to identify the scored call.

Another example embodiment may include an apparatus that includes a processor configured to identify a call scheduled for a scheduled time comprising a calling party profile and a called party profile, identify one or more calling party flags associated with the calling party profile and one or more called party flags associated with the called party profile, establish a call connection between a calling party device and a called party device at the scheduled time to conduct the call, record call content identified during the call, process the call content of the recorded call to identify call content compliance based on the calling party flags and the called party flags, score the call based on the identified call content compliance, and a processor configured to update one or more of the called party profile and the calling party profile to identify the scored call.

Another example embodiment includes a non-transitory computer readable storage medium configured to store instructions that when executed cause a processor to perform, identifying a call scheduled for a scheduled time comprising a calling party profile and a called party profile, identifying one or more calling party flags associated with the calling party profile and one or more called party flags associated with the called party profile, establishing a call connection between a calling party device and a called party device at the scheduled time to conduct the call, recording call content identified during the call, processing the call content of the recorded call to identify call content compliance based on the calling party flags and the called party flags, scoring the call based on the identified call content compliance, and updating one or more of the called party profile and the calling party profile to identify the scored call.

DETAILED DESCRIPTION OF THE APPLICATION

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

Example embodiments provide for methods, processes, devices, systems and non-transitory computer readable mediums which execute instructions to manage meetings, such as scheduled events, conferences, in-person meetings, online meetings, telephonic meetings, messaging meetings conducted over a user interface, etc. The meetings are generated based on scheduled meetings times stored in the meeting database 110 and the profiles of the employee or caller 104 and the customer profiles 102 of the callees/patients. The meeting content is analyzed and processed according to a comparison with known caller and/or callee flags. The flags are the basis of scoring the meetings for meeting compliance. As flags are identified in the content, the score may increase. The score may also decrease as the terms are identified to be in violation of the flags or other content rules.

Figure 1:
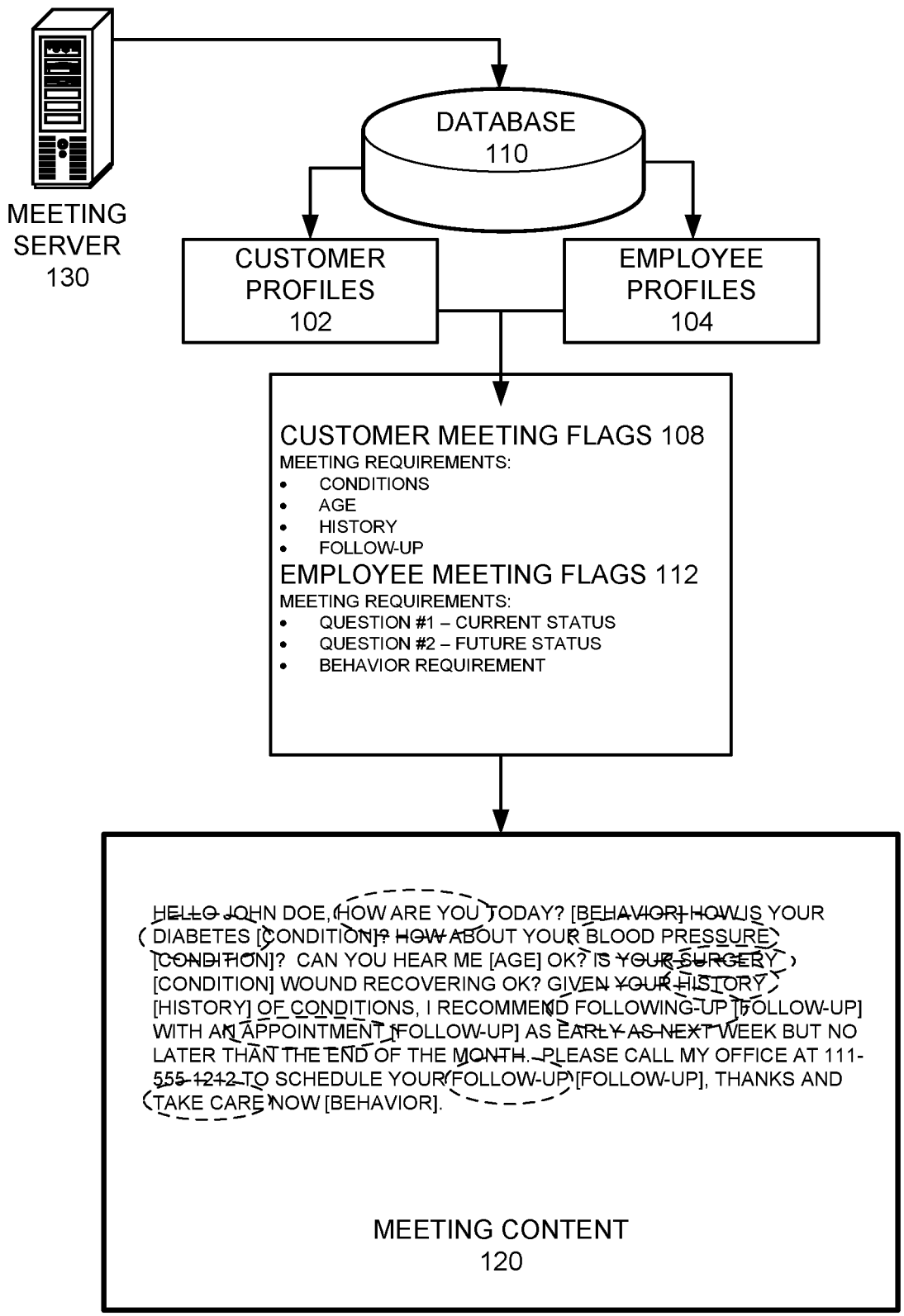
FIG. 1 illustrates an example network configuration for managing meetings and communication content according to example embodiments.

FIG. 1 illustrates a call management network configuration 100. Referring to FIG. 1, the meeting server 130 may store meetings scheduled for certain times. The server may include a database 110 which stores customer profiles 102 and employee profiles 104. In an enterprise environment, the customers may be medical patients and the employees may be physicians. The pairings for meetings may include a particular patient requiring a call from a particular physician at a particular time. For example, when a patient has recently undergone a doctor visit or other event, such information stored in the database 110 may update the customer profile of the patient to require a follow-up phone call to discuss a recently identified condition. The flags set for a patient may include requirements for any communication, such as talking slowly when the patient is above a threshold age, asking the patient certain questions, confirming the patient will follow-up in a particular time period, etc.

In this example, the customer profile has a set of flags 108 each of which will require documented discussions. The flags in this example are required for 'conditions' of the patient, 'age', 'history' and 'follow-up' requirements. In operation, when the doctor calls the patient, the content captured during the call may be stored in memory as an audio file, which is converted to a text file via a voice to text data processing application. Once the content is call/communication content is captured, the customer meeting flags 108 may be used as the basis to process the content and tag terms and phrases which match the customer flags, such as conditions, age, history and follow-up. For example, a customer may be a patient that is older in age, has certain chronic conditions, has a history of medical problems/conditions/medications and is in need of a follow-up visit with every visit. In this case, the words, terms and phrases identified from the meeting content 120 are processed to match to any of the customer/patient flags 108. The matching words and phrases which are relevant are tagged for scoring purposes, for example, the file may be modified to include a flag tag, which can be used for scoring. Certain tags and their corresponding flags may be weighted higher than others, for example, 1-point, 2-points, 3-points, etc. For purposes of this example, the flags and tags will be identified as 1-point for each instance identified in the meeting content.

The meeting may be a phone call, conference call, application message/text session, text messaging for a mobile device, e-mail, online communication session, mobile device application, etc. The content that is collected during the meeting is stored in a data file, such as a text file. The parsed or tagged terms which match the relevant flags are tagged for scoring purposes. The employee, such as a doctor at a hospital may also have certain flags 112 in his or her profile 104. The flags for the employee may be based on areas requiring improvement within the employee's engagement actions during meetings, for example, the employee may be in need of more comprehensive discussion topics, such as a better bedside manner, more questions asked, listening to the patient's responses, etc. In this example, the employee flags may be to ask questions for a current status, future status and a behavior requirement to improve niceness, sincerity and to avoid abruptness and insincerity. For example, the phrase "take care now" indicates an optimal behavior flag requirement. More examples of the flags matching the content are discussed in FIG. 2. The term 'flag' may be used to indicate a matching category of terms, such as a word or phrase and any similar variations which are known to be similar in meaning to any of the words or phrases which are paired to that particular flag.

Figure 2:
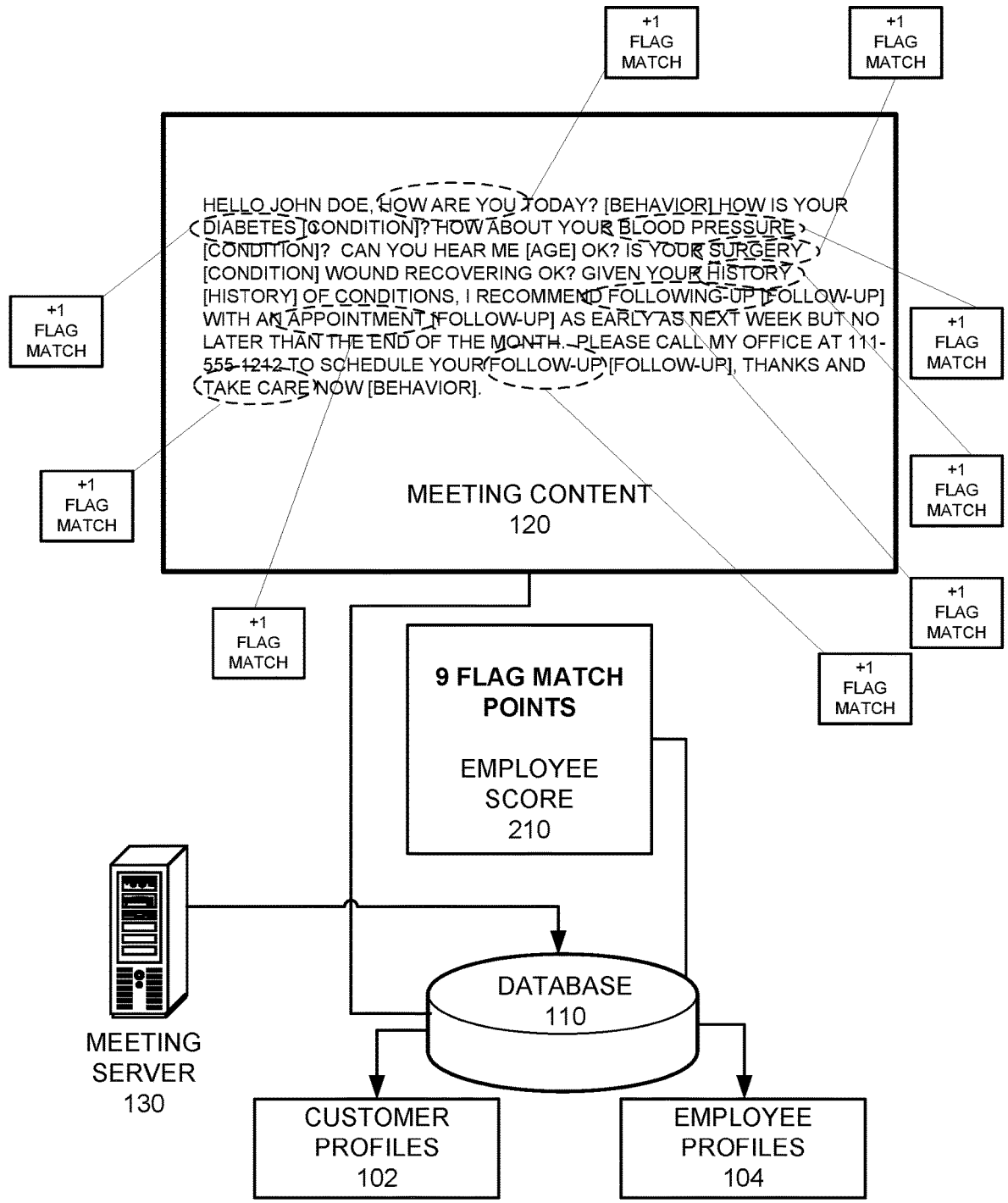
FIG. 2 illustrates an example meeting content processing configuration according to example embodiments.

FIG. 2 illustrates an example meeting content processing configuration according to example embodiments. Referring to FIG. 2, the example 200 provides the meeting content being parsed and processed word by word to match those words and phrases which are similar in contextual meaning to the flags which are used as the basis for scoring and compliance. For example, a flag may be defined by a category or title, such as 'conditions', however, that flag may be based on a larger grouping of words and phrases as potential matches to the actual meeting content 120. Each tagged match may be scored according to a scoring model, such as +1 for a regular match, +2 or more for a higher weighted match, such as a match to a more important flag, etc. Both flags for the customer and the employee may be utilized when scoring, the scores may be combined or separate to make one combined employee score 210. In this example, the total flags identified in the content as having matches yielded 9 points. The score may be stored in the employee profiles 104 and/or the customer profiles 102 for audit purposes in the event that an employee or customer needs to have their records checked for compliance with enterprise standards. In the event that a term or phrase is not matched to a flag, no score will be awarded. In the event that an inappropriate term or phrase is used, the score may be decremented. A total score may be compared to a threshold score and when the total score is equal to or above the threshold score then the meeting may be deemed a success. However, when the score is not sufficient then the meeting may be deemed insufficient and a notification may be sent to the employee, the employee's supervisor, etc. The notification may indicate the score and which flags were and were not addressed by the content. Also, any inappropriate words and phrases may be identified as well as part of the meeting summary.

Figure 3:
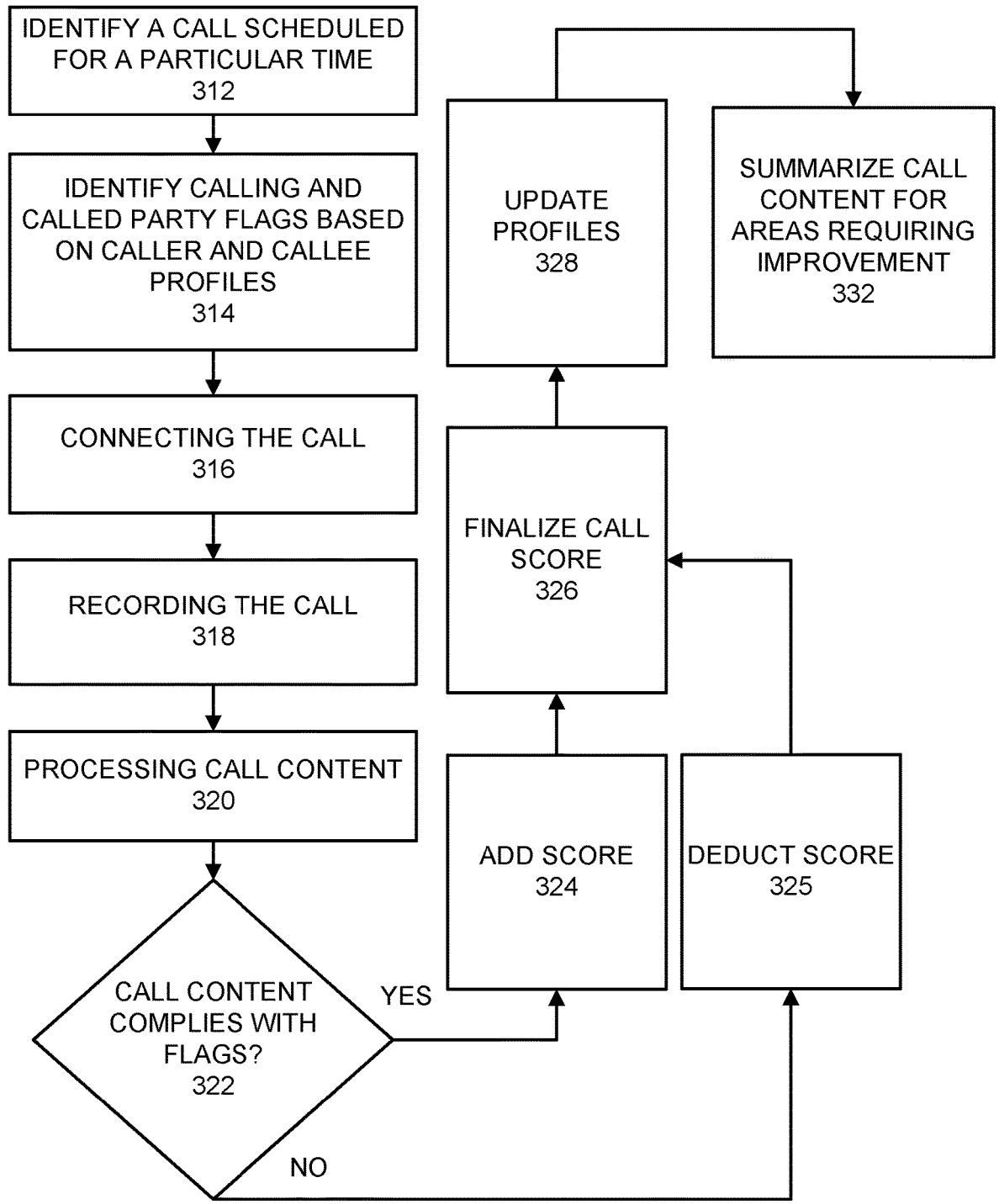
FIG. 3 illustrates an example flow diagram of a meeting managing configuration according to example embodiments.

FIG. 3 illustrates an example flow diagram of a meeting managing configuration according to example embodiments. Referring to FIG. 3, the flow diagram 300 provides a process for managing a call/meeting engagement and processing the content of the meeting for compliance measurement purposes. The process may begin with identifying a call scheduled for a particular time 312, and identifying one or more calling party flags associated with the calling party profile and one or more called party flags associated with the called party profile 314, when a meeting is about to be setup and connected. The meeting may be a call or other communication session. The meeting may be connected 316 between the employee and the customer. The content of the meeting may be recorded 318, stored in memory and the call content is processed 320 to identify flag matching content. The process may also include determining whether the content is in compliance with the flags 322, if so, the score is summed for all matching flags 324 and finalized 326 when the content is completely analyzed for relevant terms. When the content does not comply or is deemed inappropriate, the score can be deducted 325. The final score is used to update the profiles 328 and the call content is summarized for areas of the content and flags which are still requiring improvements, such as forgotten words and phrases which should have been spoken or addressed during the meeting 332.

The process may also include processing of the call content of the recorded call/meeting to identify call content compliance based on the calling party flags and the called party flags by parsing a plurality of words and phrases from the call content, and comparing the plurality of words and phrases to the calling party flags and the called party flags to identify whether content from the plurality of words and phrases match one or more of the calling party flags and the called party flags. The process may also include increasing a call score associated with the calling party profile when one or more of the plurality of words and phrases are matched to the calling party flags, and increasing a call score associated with the called party profile when one or more of the plurality of words and phrases are matched to the called party flags. The scores for both parties may be combined into one score for employee compliance purposes. The process may also include summing the increased call score associated with the calling party and the call score associated with the called party to create a final call score, determining whether the final call score is above a predetermined threshold value, and when the final call score is above the predetermined threshold value, designating the final score a satisfactory score. The process may also include determining whether the final call score is above a predetermined threshold value, and when the final call score is not above the predetermined threshold value, designating the final score an unsatisfactory score. Also, the process includes identifying which of the called party flags and the calling party flags were not matched to the one or more of the plurality of words and phrases, creating a summary of content which was supposed to be in the content but which was not included in the call content, transmitting a notification to the calling party with the summary of the content which has not included in the call content.

Figure 4:
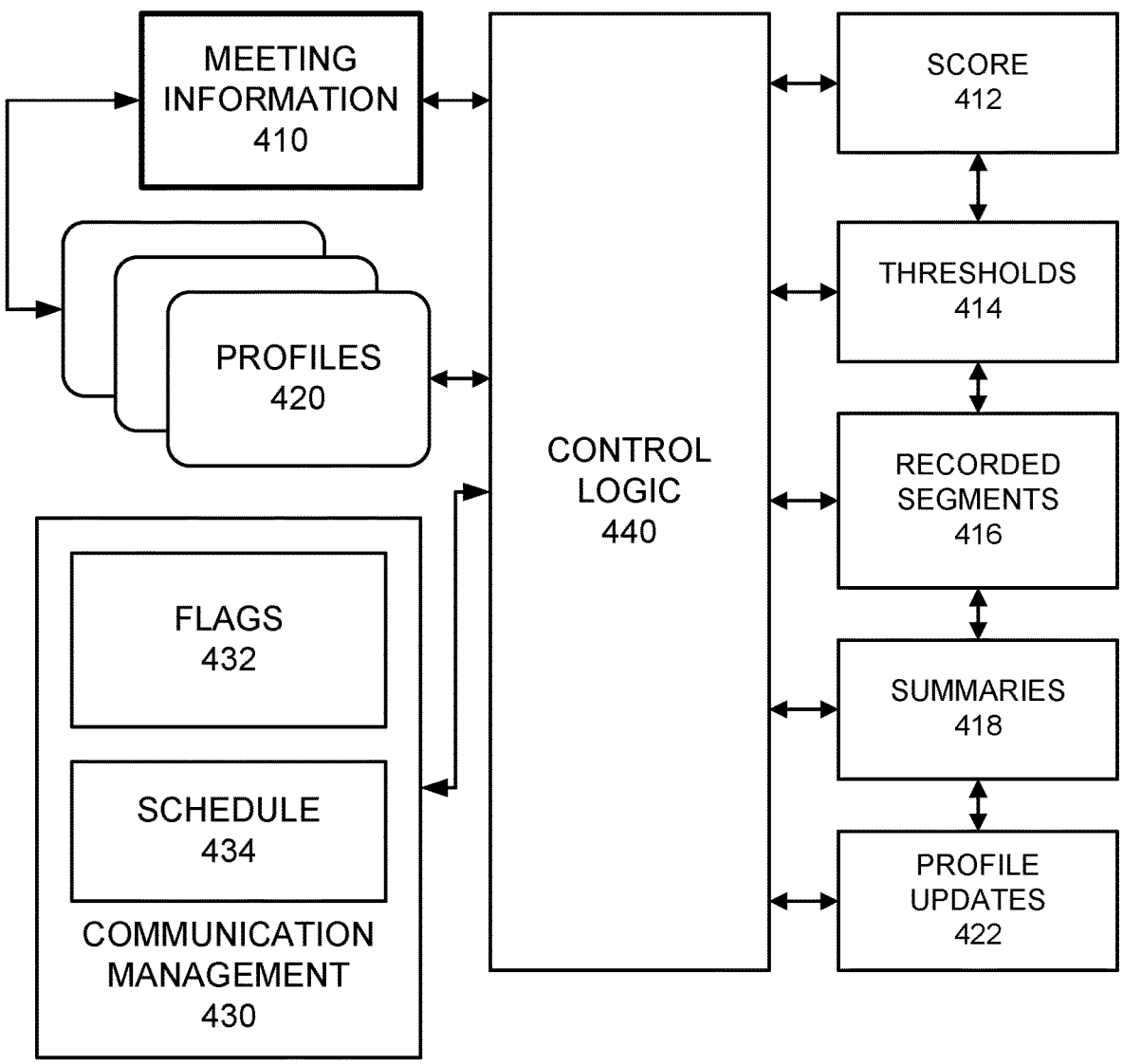
FIG. 4 illustrates an example logic control module configured to perform meeting management parameter input and output according to example embodiments.

FIG. 4 illustrates an example logic control module configured to perform meeting management parameter input and output according to example embodiments. Referring to FIG. 4, the logic example 400 includes a logic module 440 such as a processor or other computing entity. The meeting information 410 may be the scheduled meeting time, the parties to the meeting, etc. The profiles 420 may be loaded as well to identify the flags 432 to be implemented during post call processing. The schedule 434 may be a set of times and parties to include in subsequent meetings/calls. A communication management device or module 430 may manage the calls and data setup for the scheduled meetings. The output of the logic module 440 may include a score 412, thresholds used to compare to the score 414, recorded segments 416 from the meeting, summaries 418 of the meeting results and scores and profile updates 422 to reflect the scores and results of the meeting content processing.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 5 illustrates an example network element 500, which may represent any of the above-described network components of the other figures.

Figure 5:
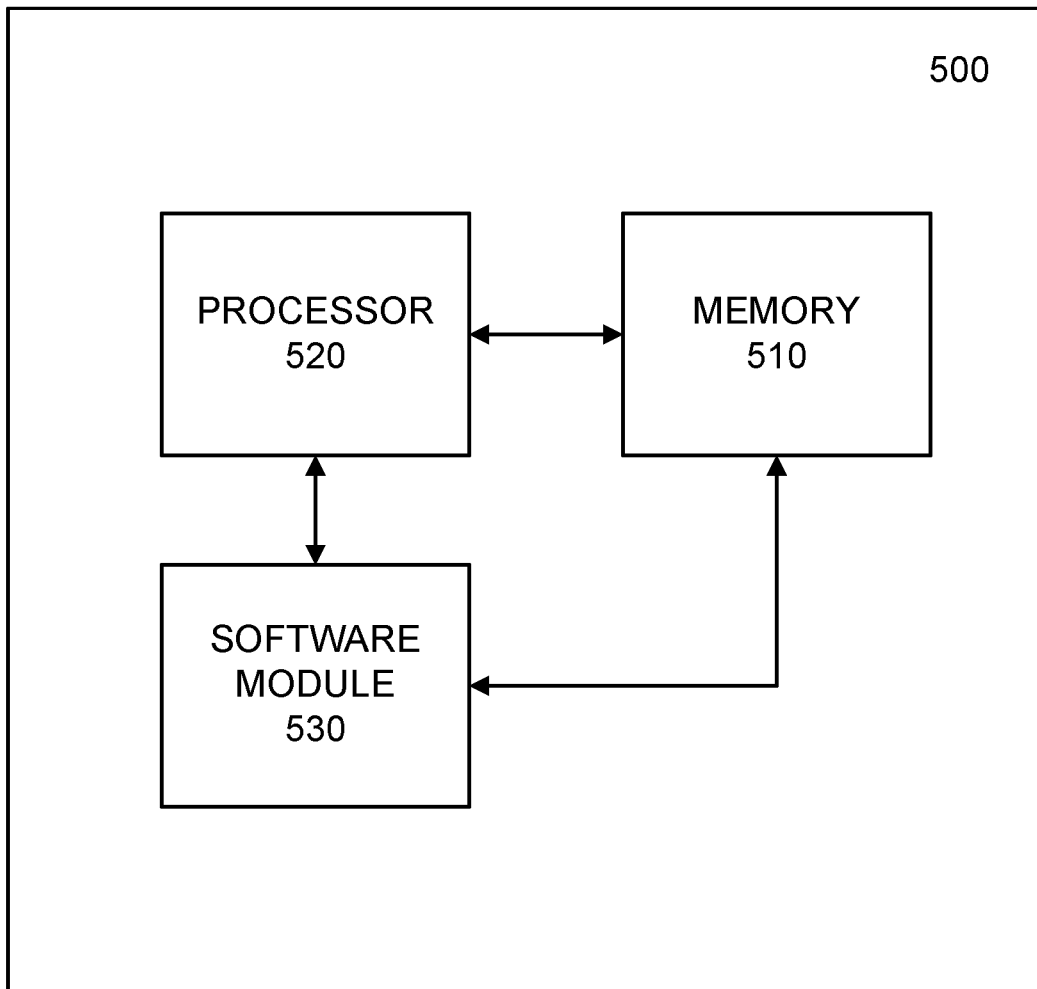
FIG. 5 illustrates an example network entity device configured to store instructions, software, and corresponding hardware for executing the same, according to example embodiments of the present application.

As illustrated in FIG. 5, a memory 510 and a processor 520 may be discrete components of the network entity 500 that are used to execute an application or set of operations. The application may be coded in software in a computer language understood by the processor 520, and stored in a computer readable medium, such as, the memory 510. The computer readable medium may be a non-transitory computer readable medium that includes tangible hardware components in addition to software stored in memory. Furthermore, a software module 530 may be another discrete entity that is part of the network entity 500, and which contains software instructions that may be executed by the processor 520. In addition to the above noted components of the network entity 500, the network entity 500 may also have a transmitter and receiver pair configured to receive and transmit communication signals (not shown).

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
identifying a call scheduled for a scheduled time comprising a calling party profile associated with a calling party and a called party profile associated with a called party;
identifying one or more calling party flags associated with the calling party profile and one or more called party flags associated with the called party profile;
recording call content identified during the call;
processing the call content of the recorded call to identify one or more words or one or more phrases spoken during the call;
determining that the one or more words or the one or more phrases spoken during the call match one or more predetermined words or one or more predetermined phrases, the one or more predetermined words or the one or more predetermined phrases corresponding to at least one of the one or more calling party flags or the one or more called party flags;
generating a score based on the match between the words spoken during the call and the one or more predetermined words, the score indicating compliance the call content with both the one or more calling party flags or the one or more called party flags;
identifying which of the called party flags and the calling party flags were not matched to the one or more words or the one or more phrases;
creating a summary of content that was not included in the call content; and
transmitting a notification to the calling party with the summary.

2. The method of claim 1, further comprising:
increasing a call score associated with the calling party profile when the one or more words or the one or more phrases are matched to the calling party flags; and
increasing a call score associated with the called party profile when the one or more words or the one or more phrases are matched to the called party flags.

3. The method of claim 2, further comprising:
summing the increased call score associated with the calling party and the call score associated with the called party to create a final call score.

4. The method of claim 3, further comprising:
determining whether the final call score is above a predetermined threshold value; and
when the final call score is above the predetermined threshold value, designating the final score a satisfactory score.

5. The method of claim 3, further comprising:
determining whether the final call score is above a predetermined threshold value; and
when the final call score is not above the predetermined threshold value, designating the final score an unsatisfactory score.

6. An apparatus comprising:
a processor configured to:
identify a call scheduled for a scheduled time comprising a calling party profile associated with a calling party and a called party profile associated with a called party;
identify one or more calling party flags associated with the calling party profile and one or more called party flags associated with the called party profile;
record call content identified during the call;
process the call content of the recorded call to identify one or more words or one or more phrases spoken during the call;

determine that the one or more words or the one or more phrases spoken during the call match one or more predetermined words or one or more predetermined phrases, the one or more predetermined words or the one or more predetermined phrases corresponding to at least one of the one or more calling party flags or the one or more called party flags;

generate a score based on the match between the words spoken during the call and the one or more predetermined words, the score indicating compliance the call content with both the one or more calling party flags or the one or more called party flags;

identify which of the called party flags and the calling party flags were not matched to the one or more words or the one or more phrases;

create a summary of content that was not included in the call content; and transmit a notification to the calling party with the summary.

7. The apparatus of claim 6, wherein the processor is further configured to:

Increase a call score associated with the calling party profile when the one or more words or the one or more phrases are matched to the calling party flags; and Increase a call score associated with the called party profile the one or more words or the one or more phrases are matched to the called party flags.

8. The apparatus of claim 7, wherein the processor is further configured to:

sum the increased call score associated with the calling party and the call score associated with the called party to create a final call score.

9. The apparatus of claim 8, wherein the processor is further configured to:

determine whether the final call score is above a predetermined threshold value; and when the final call score is above the predetermined threshold value, designate the final score a satisfactory score.

10. The apparatus of claim 8, wherein the processor is further configured to;

determine whether the final call score is above a predetermined threshold value; and when the final call score is not above the predetermined threshold value, designate the final score an unsatisfactory score.

11. A non-transitory computer readable storage medium configured to store one or more instructions that when executed by a processor cause the processor to perform:

identifying a call scheduled for a scheduled time comprising a calling party profile associated with a calling party and a called party profile associated with a called party;

identifying one or more calling party flags associated with the calling party profile and one or more called party flags associated with the called party profile;

recording call content identified during the call;

processing the call content of the recorded call to identify one or more words or one or more phrases spoken during the call;

determining that the one or more words or the one or more phrases spoken during the call match one or more predetermined words or one or more predetermined phrases, the one or more predetermined words or the one or more predetermined phrases corresponding to at least one of the one or more calling party flags or the one or more called party flags;

generating a score based on the match between the words spoken during the call and the one or more predetermined words, the score indicating compliance the call content with both the one or more calling party flags or the one or more called party flags;

identifying which of the called party flags and the calling party flags were not matched to the one or more words or the one or more phrases;

creating a summary of content that was not included in the call content; and transmitting a notification to the calling party with the summary.

12. The non-transitory computer readable storage medium of claim 11, wherein the one or more instructions further cause the processor to perform:

increasing a call score associated with the calling party profile when the one or more words or the one or more phrases are matched to the calling party flags; and increasing a call score associated with the called party profile the one or more words or the one or more phrases are matched to the called party flags.

13. The non-transitory computer readable storage medium of claim 12, wherein the one or more instructions further cause the processor to perform:

summing the increased call score associated with the calling party and the call score associated with the called party to create a final call score.

14. The non-transitory computer readable storage medium of claim 13, wherein the one or more instructions further cause the processor to perform:

determining whether the final call score is above a predetermined threshold value;

when the final call score is above the predetermined threshold value, designating the final score a satisfactory score; and when the final call score is not above the predetermined threshold value, designating the final score an unsatisfactory score.

* * * * *